United States Patent [19]
Hart et al.

[11] Patent Number: 5,569,205
[45] Date of Patent: Oct. 29, 1996

[54] MULTIPORT TROCAR

[76] Inventors: Charles C. Hart, Huntington Beach; Vincent C. Tangherlini, Rancho Santa Margarita, both of Calif.

[21] Appl. No.: 275,620

[22] Filed: Jul. 14, 1994

[51] Int. Cl.$^6$ ........................ A61M 39/22; A61M 39/26
[52] U.S. Cl. ........................................ 604/167; 604/169
[58] Field of Search ..................... 604/167, 256, 604/169

[56] References Cited

U.S. PATENT DOCUMENTS

| | | |
|---|---|---|
| 3,994,287 | 11/1976 | Turp et al. . |
| 4,112,932 | 9/1978 | Chiulli . |
| 4,180,068 | 12/1979 | Jacobsen et al. . |
| 4,379,458 | 4/1983 | Bauer et al. . |
| 4,601,710 | 7/1986 | Moll . |
| 4,654,030 | 3/1987 | Moll et al. . |
| 4,869,717 | 9/1989 | Adair . |
| 4,929,235 | 5/1990 | Merry et al. ............. 604/167 |
| 4,931,042 | 6/1990 | Holmes et al. . |
| 5,066,288 | 11/1991 | Deniega et al. . |
| 5,116,353 | 5/1992 | Green . |
| 5,197,955 | 3/1993 | Stephens et al. . |
| 5,211,633 | 5/1993 | Stouder, Jr. ............. 604/167 |
| 5,269,763 | 12/1993 | Boehmer et al. .......... 604/167 |
| 5,273,545 | 12/1993 | Hunt et al. ............. 604/167 |
| 5,300,036 | 4/1994 | Mueller et al. . |

FOREIGN PATENT DOCUMENTS

0479130  8/1992  European Pat. Off. .

*Primary Examiner*—Paul J. Hirsch
*Attorney, Agent, or Firm*—Richard L. Myers

[57] ABSTRACT

A trocar adapted to extend across the body wall into a body cavity, and to form a seal around an instrument inserted through the trocar comprises a cannula having a first axis extending between a proximal end and a distal end. A valve housing attached to the proximal end of the cannula forms a working channel with the cannula and includes a rigid housing portion and a flexible housing portion. First and second septum valves are formed in an end wall of the flexible housing portion and form separate valve sets with associated zero closure valves disposed within the valve housing. The valve sets are sized and configured to accommodate different ranges of instrument diameters. The first and second septum valves are offset from the axis of the cannula in their natural positions but are movable to positions more aligned with the axis of the cannula, due to elastomeric characteristics of the flexible housing portions. With multiple valve sets, the trocar can accommodate the simultaneous insertion of two instruments, as well as a full range of instrument diameters.

25 Claims, 4 Drawing Sheets

MULTIPORT TROCAR

BACKGROUND OF THE INVENTION

1. Field of the Invention

This invention relates generally to surgical access devices, such as trocars, which are adapted to provide access across a body wall and into a body conduit or cavity.

2. Discussion of the Prior Art

Trocars of the past have typically included a cannula and a valve housing which together define an access or working channel for various surgical instruments. The cannula has been formed in the configuration of an elongate rigid cylinder which has been inserted, with the help of an obturator, into a body cavity, such as the abdominal cavity to provide access across a body wall, such as the abdominal wall.

In a typical abdominal laparoscopic surgery, the abdomen is insufflated to pressurize and thereby enlarge the cavity within which a surgical procedure is to be performed. Various instruments used in the procedure have been inserted, previously one at a time, through the working channel of the trocar to perform the surgery. In order to maintain the insufflation pressure when the instrument is inserted through the trocar, a valve has been provided in the housing to form a seal around the instrument. These instrument valves have typically been provided in the form of septum valves. When the instrument is removed, a zero closure valve has typically been provided to seal the trocar in order to maintain the insufflation pressure.

A septum valve similar to that disclosed and claimed by applicant in copending application Ser. No. 08/051,609 filed Apr. 23, 1993 and entitled Seal Assembly for Access Device is typical of the instrument valves. A typical zero closure valve might be in the form of a double duck bill valve such as that disclosed in the same application which is incorporated herein by reference.

Instruments vary in size and diameter. While the zero closure valves of the past can accommodate a relatively wide range of diameters, the septum valves are generally capable of stretching only a nominal amount to accommodate larger diameters. Accordingly, these valve sets are generally limited as to the size of instrument which they can accommodate. Attempts have been made to increase the range of septum valves by providing levers which prestretch the valve in order to reduce some of the friction forces. These universal septum valves, such as those disclosed and claimed by applicant in U.S. Pat. No. 5,209,737, are relatively complex in structure but nevertheless are able to accommodate a wide range of instruments.

In trocars of the past, the septum valves and zero closure valves have been formed as a valve set. This set has typically been configured along a common axis which extends through the opening of the septum valve, the zero closure valve, and the cannula.

In the past, only a single valve set was provided in the trocar. This necessitated that instruments used with the trocar be inserted only one at a time. Thus a first instrument would be inserted through the septum valve and the zero closure valve to gain access to the abdominal cavity. With the instrument in place, the septum valve would maintain the insufflation pressure. Once the first instrument was removed, this insufflation pressure was maintained by the zero closure valve. Only upon removal of the first instrument could a second instrument be inserted through the same septum valve and the same zero closure valve.

When an instrument was required that had a diameter outside the range of a particular valve set, the entire trocar had to be replaced with one which could accommodate a different range of diameters. In some cases alternative septum valves were provided each of which functioned with the same zero closure valve but accommodated a different range of instrument diameters. Even where the trocars of the past provided for alternative valve sets, only a single instrument could be inserted at a time.

SUMMARY OF THE INVENTION

These deficiencies of the prior aft have been overcome with the present invention which provides for the insertion of two or more instruments into the same trocar at the same time. This trocar which provides for a seal assembly having multiple valve sets in a single valve housing, is significantly simplified so that manufacturing costs are greatly reduced.

Each of the valve sets in a preferred embodiment accommodates a different range of instrument sizes so that only a single trocar and seal assembly is required in order to accommodate all possible instrument sizes. Thus, a single simplified trocar can accommodate not only a full range of instrument sizes, but can even accommodate multiple instruments simultaneously. Not only is the single trocar less expensive to manufacture, but the number of assemblies and trocars required for a given surgical operation is also reduced. This will be greatly appreciated in a cost sensitive marketplace where as many as one million laparoscopic surgeries are performed annually in the United States, each requiring as many as four to six trocars per surgery.

Each of the valve sets is provided with characteristics for forming an instrument seal as well as a zero closure seal. These characteristics can be provided for the smallest range of instruments, by a single septum valve which additionally has zero closure characteristics. For larger valve sets, a septum valve is combined with a zero closure valve in each of the sets. In an embodiment wherein the cannula has a first axis, the septum valve a second axis, and the zero closure valve a third axis, at least one of the second and third axes is offset from the first axis. It may also be desirable to offset the Second axis of the second septum valve from the third axis of the zero closure valve in order to accommodate more valve sets in the single valve housing. In these embodiments, the zero closure valves can be formed in any manner associated with the prior art, but the double duck bill valve configuration is preferred.

In one aspect of the invention, a trocar is adapted to extend across a body wall into a body cavity, and to form a seal around an instrument inserted through the trocar into the body cavity. The trocar comprises a cannula forming an elongate passage and a valve housing disposed at a proximal end of the trocar. A valve assembly is disposed relative to the housing and includes a first valve set forming a first working channel with the passage of the cannula and a second valve set forming a second working channel with the passage of the cannula. The first valve set includes a first septum valve and a first zero closure valve each disposed along the first working channel. The second valve set includes a second septum valve and second zero closure valve each disposed along the second working channel. The trocar further comprises means for further supporting at least one of the first septum valve and the second septum valve relative to the housing in a "floating" relationship with the cannula.

In an additional aspect of the invention, a trocar assembly includes a cannula having an axis extending between a proximal end and a distal end. A housing disposed at the distal end of the cannula includes a rigid housing portion fixed to the cannula and an axially compressible elastomeric housing portion disposed proximally of the rigid housing portion. Together the rigid and elastomeric housing portions form a working channel with the cannula of the trocar. This channel is sized and configured to receive an obturator having a shaft with an axis extending to a sharp distal tip. When the obturator is operatively disposed, this distal tip extends beyond the distal end of the cannula. The trocar assembly includes means associated with the shaft of the obturator and at least one of the cannula and the rigid housing portion for preventing insertion of the obturator into the cannula beyond the operative position of the obturator in order to avoid substantial axial compression of the elastomeric housing portion.

In a further aspect of the invention, a trocar assembly includes a cannula having a first axis and a valve housing forming a working channel with the cannula. A first septum valve is disposed relative to the housing and includes portions defining a first opening having a second axis. A second septum valve is disposed relative to the housing and has portions defining a second opening having a third axis. At least one of the second axis of the first septum valve and the third axis of the second septum valve is offset from the first axis of the cannula.

In still a further aspect of the invention, a trocar includes a cannula having a first axis and a septum valve disposed along the working channel of the trocar and forming an opening having a second axis. The septum valve is formed of an elastomeric material stretchable between a first natural position wherein the opening of the septum valve is disposed with the Second axis offset from the 10 first axis of the cannula, and a second stretched position wherein the second axis of the septum valve is generally aligned with the first axis of the cannula. Means is provided for supporting the septum valve relative to the cannula to permit movement of the septum valve from the first natural position to the second stretched position without substantial deformation of the opening of the septum valve.

These and other features and advantages of the invention will become more apparent with the description of preferred embodiments and reference to the associated drawings.

DESCRIPTION OF PREFERRED EMBODIMENTS

Figures 1, 2:
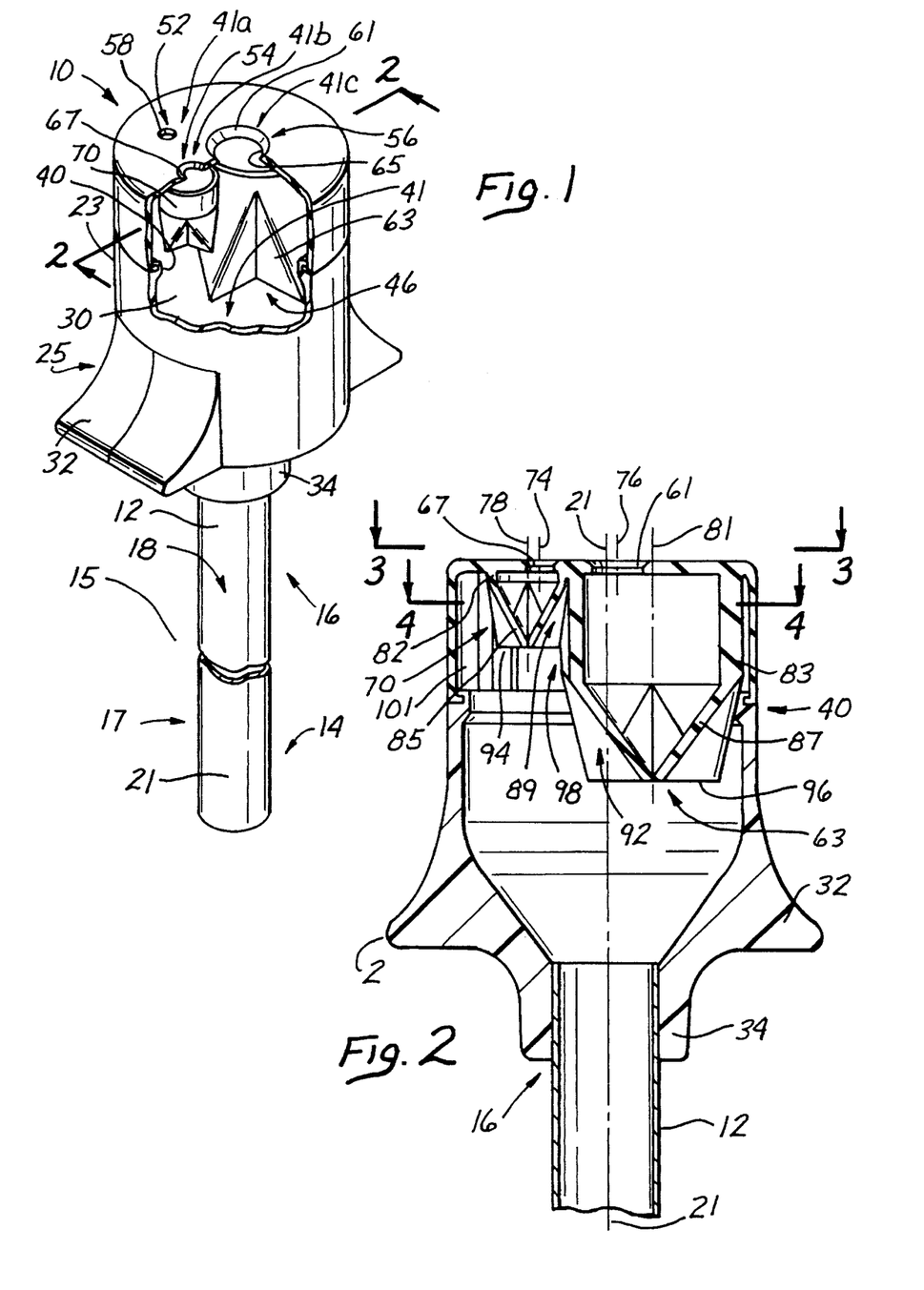
FIG. 1 is a perspective view of a preferred embodiment of the trocar of the present invention.
FIG. 2 is an axial cross-section view taken along lines 2—2 of FIG. 1, and illustrating a preferred embodiment of a valve housing and associated valve assembly.

A multiport trocar is illustrated in FIG. 1 and designated generally by the reference numeral 10. The trocar 10 is representative of any access device including a cannula 12 which is in the form of a hollow elongate cylinder having a distal end 14 and a proximal end 16. It is this cannula 12 which is sized and configured to extend across a body wall, such as the abdominal wall 15, into a body conduit or cavity, such as a blood vessel or the abdominal cavity 17. The cannula 12 is preferably rigid, or semi-rigid and in preferred embodiments is formed of plastics or surgically compatible metals such as stainless steel. A passage 18 formed by the walls of the cannula 12 extends along a central axis 21.

A valve housing 23 also forms a significant part of the trocar 10. In the illustrated embodiment, the valve housing 23 includes a rigid housing portion 25 and an elastomeric housing portion 27 which together define a housing cavity 30.

The rigid housing portion 25 is preferably formed of plastic and disposed at the proximal end 16 in a fixed relationship with the cannula 12. In the illustrated embodiment, a pair of finger tabs 32 are formed as an integral part of the rigid housing portion 25 and provide means for engaging the trocar 10 and manipulating the cannula 12 into a preferred operative position. A collar 34 is disposed distally of the tabs 32 where it is sized and configured to receive the proximal end 16 of the cannula 12, as best illustrated in FIG. 2.

The elastomeric housing portion 27 is preferably formed of natural rubber and includes a cylindrical side wall 36 and an end wall 38 which are integral in a preferred embodiment. The side wall 36 is preferably centered on the axis 21 of the cannula 12 while the end wall 38 is transverse, for example perpendicular, to the axis 21. In a preferred embodiment, the side wall 36 of the elastomeric housing portion 27 is joined to and forms a seal with the rigid housing portion 25 at a circumferential joint 40.

The cavity 30 formed by the valve housing 23 is in fluid communication with the passage 18 of the cannula 12. Together this cavity 30 and passage 18 form a working channel 41 of the trocar 10. In the illustrated embodiment, this channel 41 extends from regions exterior of the trocar 10, through the end wall 38, into the housing cavity 30, and through the passage 18 and the distal end 14 of the cannula 12. Thus the trocar 10 functions as an access device so that instruments can be inserted through the seal housing 23 and the cannula 12 into the abdominal cavity 17.

In a typical laparoscopic surgery, the trocar 10 is disposed with the cannula 12 extending across the abdominal wall 15 and into the abdominal cavity 17. In order to increase the working space at the surgical site, the abdominal cavity 17 is typically pressurized or insufflated. In the trocar 10 illustrated in FIG. 3, this insufflation of the abdominal cavity 17 is implemented by use of an insufflation tube 45 which is in fluid communication with the housing cavity 30 as well as the passage 18 of the cannula 12.

After the abdominal cavity 17 is appropriately insufflated, various instruments, such as catheters, guide wires, graspers, staplers, can be inserted through the working channel 41 of the trocar 10 to perform various functions within the abdominal cavity 17. It is important in such an operation, that the insufflation pressure be maintained both when the instruments are disposed within the working channel 41 of the trocar 10, as well as when the instruments are removed from the working channel 41. Such is the function of a valve assembly 46 which is typically disposed within the housing cavity 30 or formed as part of the valve housing 23.

The valve assembly 46 of the present invention is sized and configured to accommodate a surgical instrument having substantially any diameter regardless of the size limitations of a single valve. Such instruments are represented by a catheter 48, a retractor 49 and a obturator 50 best illustrated in FIGS. 6 and 7. In the following discussion, the catheter 48, retractor 49 and obturator 50 are sometimes referred to respectively as the small, medium and large instruments 48, 49, 50, and collectively as the instruments 48, 49 and 50.

As noted, these instruments 48–50 will vary widely in diameter. For example, the small size instrument 48 might include a guidewire or catheter up to two millimeters in diameter. The medium size instrument 49 might include graspers or retractors between two and five millimeters in diameter. The large size instrument 50 might include an obturator or laparoscope having diameters as small as five millimeters and as large as eleven or twelve millimeters.

This entire range of diameters, for example from zero to eleven or twelve millimeters, can be accommodated with the single multiport trocar 10 of the present invention. In this concept, the valve assembly 46 includes at least two and preferably three or four valve sets each adapted to receive a different range of instrument sizes, and collectively to accommodate the entire range of instrument sizes. In the illustrated embodiment the valve assembly 46 includes a small valve set 52, a medium valve set 54 and a large valve set 56. These valve sets 52, 54 and 56 form, with the passage 18 of the cannula 12, three respective working channels 41a, 41b, and 41c.

Each of the valve sets 52–56 must have characteristics for forming a seal around the associated instrument 48–50 when it is operably disposed in the working channel 41, as well as characteristics for forming a seal across the working channel 41 when the associated instrument 48–50 is removed. For the small valve set 52, both of these characteristics can be provided by a single septum valve 58 which has an opening 59 small enough to close upon itself in the absence of the instrument 48, but large enough to accommodate instruments of up to about two millimeters in diameter.

The large valve set 56 is representative of the other valve sets in the valve assembly 46. This large valve set 56 includes a large septum valve 61 as well as a large zero closure valve 63. These valves 61 and 63 can be of the type disclosed in applicant's copending application Ser. No. 08/051,609 filed on Apr. 23, 1993 and entitled Seal Assembly for Access Device.

In order to accommodate a large instrument, such as the obturator 50, the large septum valve 61 is provided with a hole 65 which in its natural state has a diameter, such as about five millimeters. Forcing the instrument 50 with a diameter larger than about five millimeters through this hole 65 causes the valve 61 to expand so that it forms a tight seal with the outer surface of the instrument 50. However, when the instrument 50 is removed, the septum valve returns to its natural state leaving the hole 65 in an open state. Under these circumstances, the zero closure valve 63 is of particular importance as it fully closes in the absence of the instrument 50. This insures that the working channel 41c through the large valve set 56 is fully closed when the instrument 50 is removed.

The medium valve set 54 is similar to the large valve set 56 in its function, however, it is generally smaller in size. Thus the medium valve set 54 includes a medium septum valve 67 and a medium zero closure valve 70. As was the case with the large septum valve 61, the medium septum valve 67 has a hole 71 which is sufficiently large to accommodate medium size instruments between about two millimeters and five millimeters, for example. This medium septum valve 67 does not fully close as did the small septum valve 58, so the zero closure valve 70 is required to seal the working channel 41b through the medium valve set 54 when the instrument 49 is removed.

Figure 3:
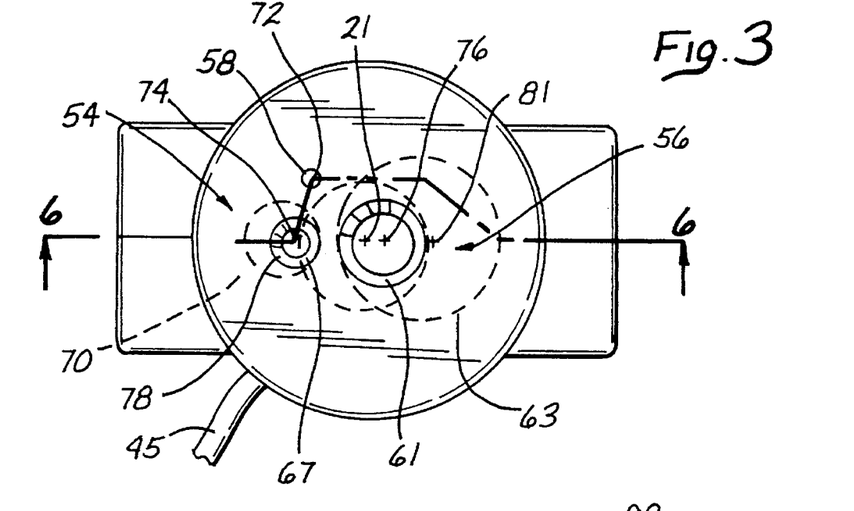
FIG. 3 is a top plan view taken along lines 3—3 of FIG. 2.

In order to accommodated the multiple valve sets 52–56 within a single valve housing 23, the lateral orientation of the respective septum valves 58, 67 and 61 in the end wall 38 can be of particular importance. With reference to FIG. 3, it will be noted that the three septum valves 58, 67 and 61 are each centered on an associated longitudinal axis 72, 74 and 76. Similarly, the 10 zero closure valves 70 and 63 are centered on respective longitudinal axes 78 and 81.

Each of the axes 72–76, associated with the respective septum valves 58, 67 and 61, is separated or off set from the axis 21 of the trocar 10 by a different distance. In the illustrated embodiment the axis 76 associated with the large septum 61 is disposed closest to the axis 21. This orientation is preferred since a larger instrument, such as the obturator 50, requires a more vertical orientation with the trocar 10 due to the fact that its diameter more closely approaches that of the cannula 12. Thus, by locating the axis 76 relatively close to the axis 21, the septum valve 61 is required to move only a small distance in order to achieve the more vertical orientation required by the large instrument 50.

Figure 6:
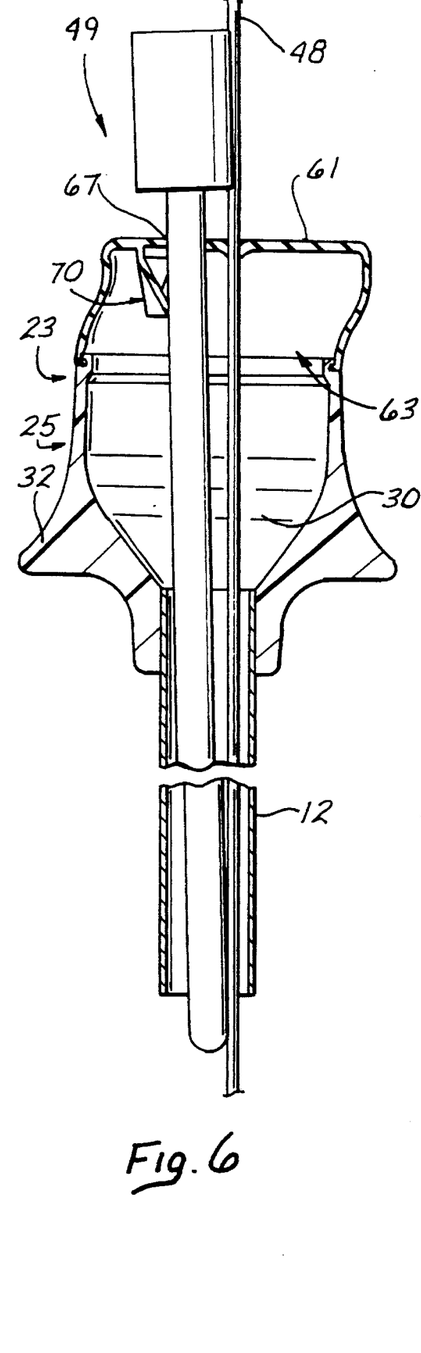
FIG. 6 is a cross-section view similar to FIG. 2 and illustrating a small sized instrument and a medium sized instrument simultaneously operatively disposed through first and second valve sets of the trocar.

As illustrated in FIG. 6, the medium sized instruments, such as the retractor 49, can pass through the cannula 12 at an angle so that the medium size instrument 49 does not require as vertical an orientation as the large instrument 50. Thus the medium septum valve 67 need not move as close to the axis 21 of the cannula 12 for operative disposition of the instrument 49. For this reason, the axis 74 of the medium septum valve 67 can be offset from the axis 21 of the cannula 12 a distance greater than that separating the axis 76 of the large septum valve 61 from the axis 21 of the cannula 12. With respect to the small septum 58, its axis 72 can be located at an even greater distance from the axis 21. Not only do small instruments, such as guidewires and the catheter 48, require very little vertical orientation, but they are often flexible so that no movement of the septum 58 is required for operative disposition of these small instruments.

For the reasons just discussed, it is important that the septumvalves 61 and 67 be located so that they can move from their natural position, in the absence of the instruments 49, 50 to a more centered position, in the presence of the instruments 49, 50. This movement must occur without substantial deformation of the septum valve 67 and 61 so that the valve portions forming the respective holes 71 and 65 can form a suitable seal with the outer surface of the instruments 49, 50.

In a preferred embodiment, this movement without deformation is accommodated by two characteristics of the trocar 10. First, the end wall 38 is formed of an elastomeric material thereby permitting the septumvalves 58, 67 and 61 to move laterally within the end wall 38. Perhaps more importantly, the side wall 36 of the housing portion 27 is also formed of an elastomeric material and is easily deflected laterally. This movement of the side wall 36 carries the entire end wall 38 to a desired position without deformation of the associated septum valve 58, 67 and 61. Thus the septum valves 58, 67 and 61 have a floating relationship with the cannula 12 which permits them to move laterally while still maintaining their properties for forming a seal with the outer surface of the associated instrument 48–50. This lateral deflection of the side wall 36 is illustrated in both FIGS. 6 and 7 for the respective instruments 49 and 50.

In the foregoing embodiment, the septum valves 58, 67 and 61 are formed in the end wall 38 of the elastomeric housing portion 27. It will be apparent, however, that these valve 58, 67 and 61 can be formed generally in any wall which is transverse to the axis 21 of the cannula 12. The resulting Valve wall can be included within the housing cavity 30 or can fore part of the valve housing 23. Nevertheless, it is generally preferred that the septumvalves 58, 67, and 61 be formed in the proximal-most wall, such as the end wall 38, of the valve housing 23.

The location of the zero closure valve 70 and 63 can also be critical in a particular embodiment. It is not required that the axes 78 and 81 associated with the zero closure valves 70 and 63 respectively, be aligned with the axes 74 and 76 of the associated septum valves 67 and 61. This alignment of valves within a valve set, which is characteristic of the prior art, is not required by the present invention. Rather the location of the zero closure valves 70 and 63 is generally dependent on two different considerations.

First, the zero closure valve 70 must be positioned such that the instrument 49 passing through the associated septum valve 67 also passes through zero closure valve 70. Similarly, the zero closure valve 63 must be positioned so that the instrument 50, passing through the associated septum valve 61 also passes through the zero closure valve 63. As can be seen from FIG. 3, this requirement is not particularly stringent so that the septum valves 67 and 61 can be located relatively close to the central axis 21 while the associated zero closure valve 70 and 63 are located relatively far from the central axis 21.

The second consideration for location of the zero closure valves 70 and 63, is based on their proximity to each other. It is important that when the medium instrument 49 is positioned within the medium valve set 54, that it not interfere with the ability of the large zero closure valve 63 seal the working channel 41c. This generally requires that the medium zero closure valve 70 be separated from the large zero closure valve 63 a distance sufficient to prevent deformation of the large zero closure valve 63.

In the illustrated embodiment, this interference with a non-associated zero closure valve 63 is of perhaps greatest concern with respect to the medium valve set 54. In this valve set 54, the medium instrument 49 will typically have a more angled disposition within the housing cavity 30 than the large instrument 50. Furthermore, the large zero closure valve 63 will typically extend further into the housing cavity 30, as illustrated in FIG. 2, making it more susceptible to interference from the medium instrument 49.

Figures 4, 5:
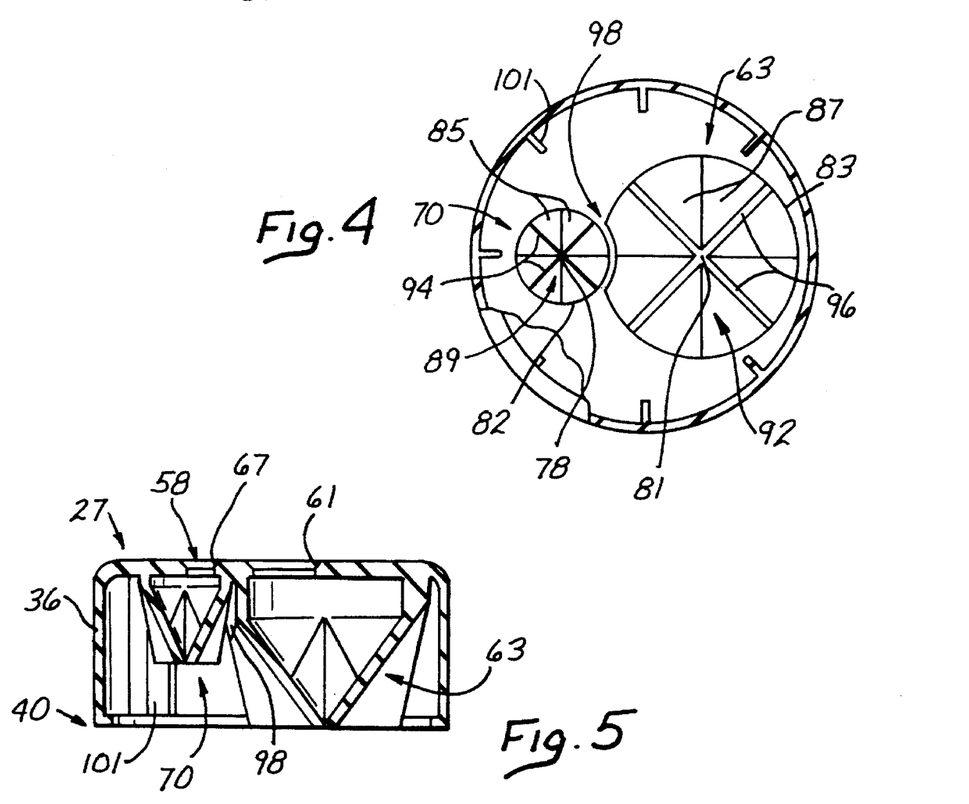
FIG. 4 is a radial cross-section view taken along lines 4—4 of FIG. 2.
FIG. 5 is an axial cross-section view similar to FIG. 2 and illustrating an additional embodiment of a valve housing.

The double duck bill valve configuration illustrated for the zero closure valves 63 and 70 is particularly beneficial in avoiding this interference. Each of these zero closure valves 70 and 63 includes respectively, a cylindrical side wall 82 and 83, and a closure structure defined by walls 85 and 87. These walls 85, 87 define lateral recesses 89, 92 as they converge to lines 94, 96, respectively, which form the cross seal associated with this type of zero closure valve. These lines 94 and 96 are best illustrated in FIG. 4. The configuration of the walls 85, 87 and the associated recesses 89, 92 and lines 94, 96 are described in greater detail in applicant's copending application Ser. No. 08/051,609.

In general, this configuration of the zero closure valves 70 and 63 facilitates a structure wherein one of the valves, such as the valve 70, can be provided with a side wall, such as the side wall 82, which is shorter than the side wall, for example the side 83, associated with the other zero closure valve, such as the valve 70. Then, a recess or indentation 98, can be formed in the other side wall, such as the side wall 83. It will be apparent that this solution will be equally appropriate with a longer side wall 82 in the medium zero closure valve 70, and an appropriate indentation, such as the indentation 98, in that side wall 82.

Another way of accommodating the close proximity of the zero closure valves 70 and 63 is to orient the associated seal lines 94 and 96 so that neither is disposed along a line interconnecting the axes 78 and 81 of the respective valve 70 and 63. Since these seal lines 94 and 96 extend to the greatest diameter of the associated walls 85 and 87 they are most susceptible to interference by an instrument 78, 80 extending through the opposite valve set 54, 56. By orienting these lines 94 and 96, as illustrated in FIG. 4, the natural recesses 89 and 92 formed between lines 94, 96 are automatically faced toward the opposing axis 78, 81.

As one contemplates an appropriate length for either of the side walls 83, 85, it must be appreciated that additional length will ultimately demand a longer valve housing 23. For comparison, it will be noted that in the embodiment of FIG. 2, the zero closure valve 63 extends beyond the joint 40 between the rigid housing portion 25 and the elastomeric housing portion 27. In an embodiment wherein the length of the seal housing 23 is to be minimized, it may be desirable to shorten the side walls 85 associated with the zero closure valve 63. This could produce an embodiment wherein neither of the zero closure valves 63 or 70 extends beyond the joint 40 between the housing portions 25 and 27.

When an instrument, such as the instruments 49 and 50, is removed from the trocar 10, it is desirable that the elastomeric housing portion 27 return to its natural state wherein its side wall 36 is coaxial with the central axis 21. This return to the natural state is facilitated in a preferred embodiment wherein the housing portion 27 is provided with a plurality of ribs 101 which extend radially and longitudinally of the side wall 36 within the housing cavity 30.

In a preferred embodiment, the entire elastomeric housing portion 27 (including the ribs 101) and the entire valve assembly 46 (including the septum valves 58, 67, 61 and the zero closure valves 70, 63) are formed as an integral structure from an elastomeric material such as latex.

Figure 7:
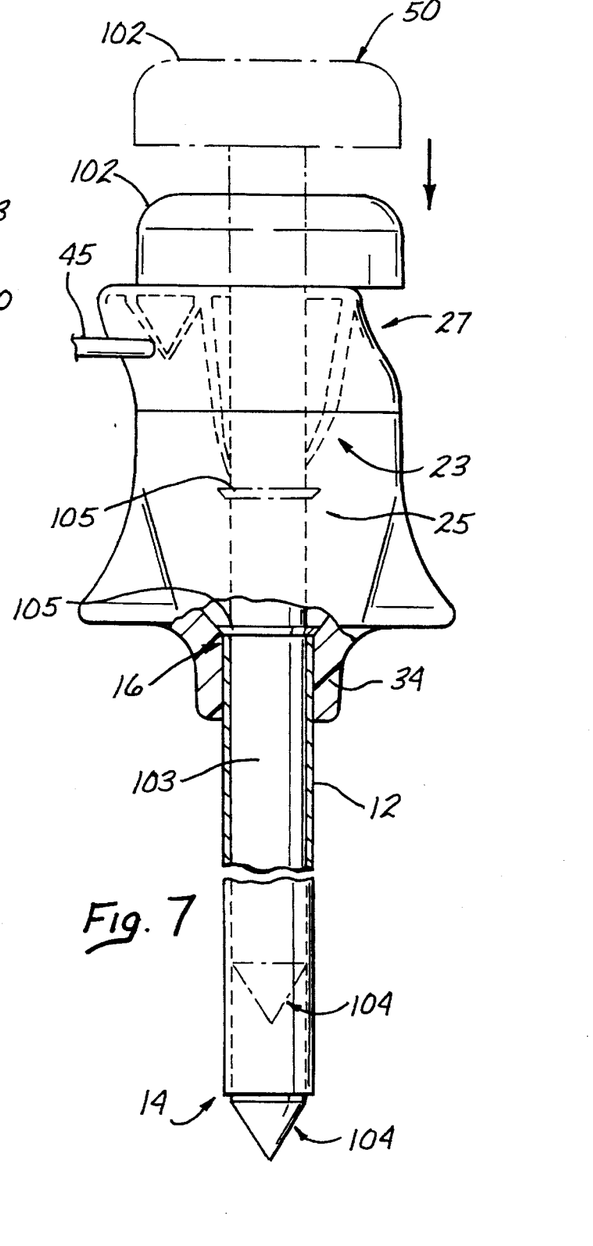
FIG. 7 is a radial cross-section view similar to FIG. 6 and illustrating a large instrument in the form of an obturator operatively disposed in the trocar.

The lateral flexibility desired for the elastomeric housing portion 27 also produces an axial flexibility which may not be desired when the trocar 10 is used with obturators of the prior art. As illustrated in FIG. 7, the obturator 50 of the present invention is typical of those of the past in that it includes a handle 102 and a shaft 103 having a sharp distal tip 104. This obturator 50 is designed for axial insertion through the valve housing 23 and into the cannula 12 as illustrated by the dotted line position in FIG. 7. Further axial movement into the cannula 12 brings the obturator 50 to an operative position where the sharp distal tip 104 of the obturator 50 extends beyond the distal end 14 of the cannula 12. This operative position is shown by the solid line position of the obturator 50 in FIG. 7. Once the obturator 50 is disposed in its operative position within the cannula 12, further axial pressure on the handle 102 is intended to force the sharp distal tip 104 through the abdominal wall 15 to position the distal end 14 of the cannula 12 within the abdominal cavity 14.

With obturators of the past, this axial pressure was directed through the handle and applied against the proximal end of the valve housing. In the present invention, however, this additional pressure on the proximal end of the housing 23 would only seek to compress the elastomeric housing portion 27. This would not only make it difficult to insure the operative disposition of the sharp tip 96 beyond the cannula 12, but also could damage the elastomeric housing portion 27.

In a preferred embodiment, illustrated in FIG. 7, the obturator 50 is provided with an enlargement or projection 105 which is fixed to the outer surface of the shaft 95. In the illustrated embodiment, the projection 105 takes the form of an annular flange which extends radially outwardly from the outer surface of the shaft 95. When the obturator 50 is inserted from its dotted line position in FIG. 7 to its solid line operative position, this projection 105 moves through the housing cavity 30 into engagement with the proximal end 16 of the cannula 12 which functions as a stop for the projection 105. Since the projection 105 is larger than the inside diameter of the cannula 12 in this embodiment, further axial movement of the obturator 50 is prevented. In this operative position of the obturator 50, the distal tip 104 of the shaft 103 extends beyond the distal end 14 of the cannula 12, but the handle 102 does not axially compress the elastomeric housing portion 27. In general, the projection 105 can be positioned along the shaft 102 at any location where it can engage part of the rigid housing portion 25, such as the collar 34, or the proximal end 16 of the cannula 12.

Figure 8:
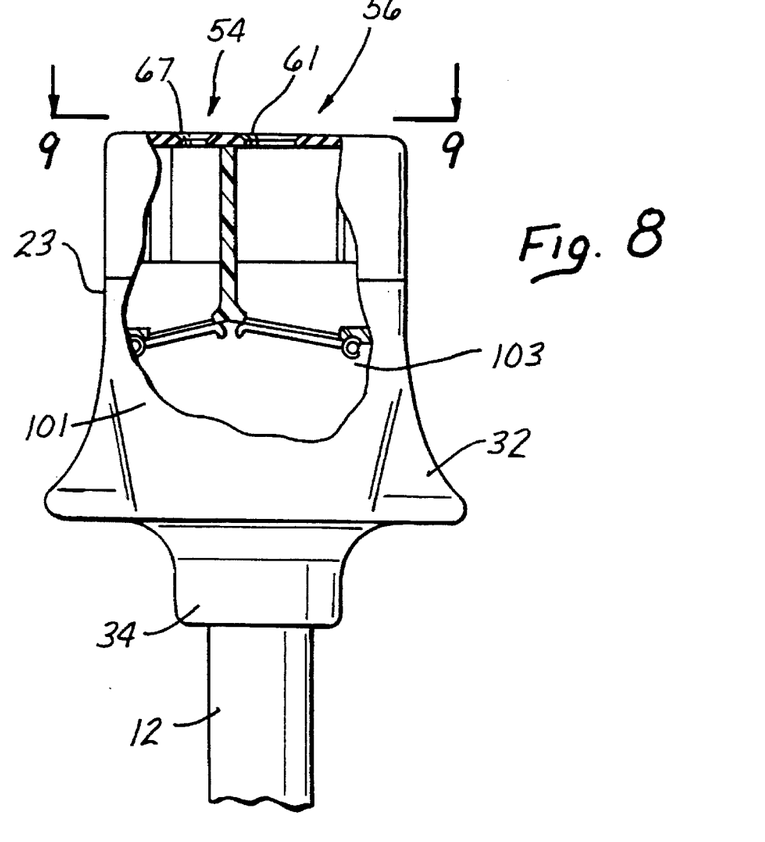
FIG. 8 is a side view partially in section of the trocar illustrating a flapper valve having zero closure characteristics in a further embodiment of the invention.
Figure 9:
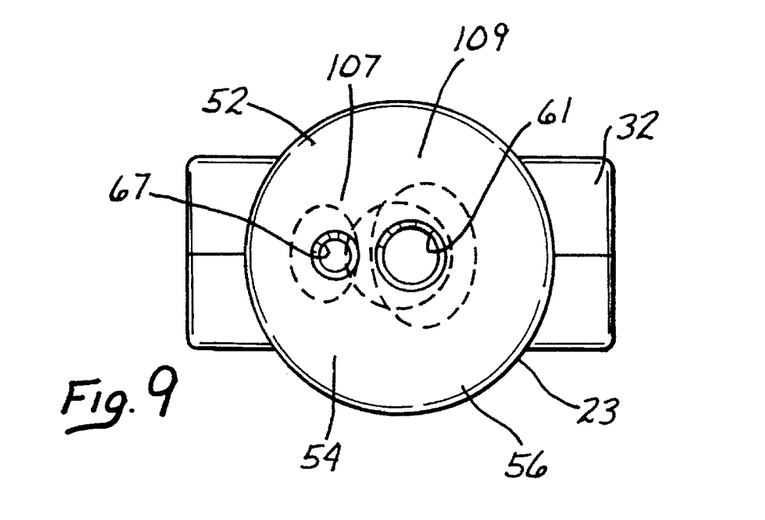
FIG. 9 is a top plan view taken along lines 9—9 of FIG. 8.

From the foregoing discussion it is apparent that the trocar 10 of this invention can accommodate all sizes of instruments from the smallest instrument, such as the catheter 48, to the largest instrument, such as the obturator 50, which can pass through the associated cannula 12. Multiple septum valves 58, 67 and 61 can be formed in any transverse wall disposed interiorly of the valve housing 23 or at the end wall 38 of the elastomeric housing portion 27. These septum valves 58, 67 and 61 can be formed at different distances from the central axis 21 in the manner previously discussed. For each of the larger valve sets, for example the medium valve set 54 and large valve set 56, a zero closure valve may be required. These valves, such as the zero closure valves 70 and 63, can be provided in any form associated with the prior art. Double duck bill valves such as those illustrated in FIGS. 1–7 are particularly appropriate for this concept. However, a separate flapper valve, such as those designated by the reference numerals 107 and 109, can be provided for the respective valve sets 54 and 56 as illustrated in FIGS. 8 and 9.

Given these wide variations, which are all within the scope of this concept, one is cautioned not to restrict the invention to the embodiments which have been specifically disclosed and illustrated, but rather encouraged to determine the scope of the invention only with reference to the following claims,

We claim:

1. An access device adapted to extend across a body wall into a body conduit or cavity and to form a seal around an instrument inserted through the device into the body conduit or cavity, the device comprising:

a cannula forming an elongate passage extending from a proximal end to a distal end of the cannula;

a valve housing disposed at the proximal end of the cannula;

a first valve set disposed relative to the housing and forming with the passage of the cannula a first working channel;

a first septum valve included in the first valve set and disposed along the first working channel;

a first zero closure valve included in the first valve set and disposed along the first working channel axially of the first septum valve;

a second valve set disposed relative to the housing and forming with the passage of the cannula a second working channel;

a second septum valve included in the second valve set and disposed along the second working channel;

a second zero closure valve included in the second valve set and disposed along the second working channel axially of the second septum valve; and means for flexibly supporting at least one of the first septum valve and the second septum valve relative to the housing in a floating relationship with the cannula.

2. The access device recited in claim 1 wherein at least one of the first and second zero closure valves is a double duck bill valve.

3. The access device recited in claim 1 wherein:

the cannula has a first axis;

the first septum valve has a second axis; and the second axis of the first septum valve is offset from the first axis of the cannula.

4. The access device recited in claim 3 wherein:

the first zero closure valve has a third axis;

the second axis of the first septum valve is offset from the first axis of the cannula a first distance;

the third axis of the first zero closure valve is offset from the first axis of the cannula a second distance; and the second distance is greater than the first distance.

5. The access device recited in claim 1 further comprising:

first housing portions having rigid properties and a fixed relationship with the cannula;

second housing portions having elastomeric properties and a floating relationship with the cannula;

the first housing portions and the second housing portions forming the valve housing of the trocar; and at least the first septum valve and the second septum valve being formed integral with the second housing portions.

6. The access device recited in claim 5 wherein the first zero closure valve and the second zero closure valve are formed integral with the second housing portion;

7. A trocar assembly including:

a cannula having an axis extending between a proximal end and a distal end of the cannula;

a rigid housing portion having a distal end and a proximal end, the distal end of the rigid housing portion having a fixed relationship with the cannula;

an elastomeric housing portion coupled to the proximal end of the rigid housing portion, the elastomeric housing portion being axially compressible;

the rigid housing portion and the elastomeric housing portion forming a valve housing and defining with the cannula a working channel of the trocar;

an obturator sized and configured for removable insertion through the working channel;

a shaft included in the obturator and having an axis extending from a proximal end to a sharp distal tip, the shaft being sized and configured for removable insertion into the cannula to an operative position wherein the distal tip of the shaft extends beyond the distal end of the cannula;

a handle of the obturator attached in a fixed relationship to the proximal end of the shaft; and means carried by the shaft of the obturator between the proximal end of the shaft and the distal end of the shaft for engaging at least one of the cannula and the rigid housing portion in order to prevent insertion of the obturator into the cannula beyond the operative position of the obturator.

8. The trocar assembly recited in claim 7 wherein the engaging means includes:

a projection disposed in a fixed relationship with the shaft of the obturator distally of the valve housing and proximally of the sharp distal tip, the projection extending laterally of the shaft a distance sufficient to prevent the projection and the shaft from extending beyond the operative position of the shaft within the cannula.

9. The trocar assembly recited in claim 8 further comprising:

a shoulder defined by one of the valve housing and the cannula at the proximal end of the cannula;

the shoulder being exposed within, the working channel and forming a stop which engages the projection of the obturator to prevent distal movement of the obturator beyond the operative position.

10. The trocar assembly recited in claim 7, further comprising a first valve and a second valve, the first valve and the second valve being integral with the elastomeric housing portion.

11. The trocar assembly recited in claim 10 wherein:

the axis of the cannula is a first axis;

the first valve has a second axis;

the second valve has a third axis; and at least one of the second axis of the first valve and the third axis of the second valve is offset from the first axis of the cannula.

12. A trocar assembly, including:

a cannula having a first axis extending between a proximal end and a distal end;

a valve housing fixed to the cannula at the proximal end of the cannula and forming with the cannula a working channel;

a valve wall included in the valve housing and having first portions disposed generally transverse to the axis of the cannula, the valve wall having elastomeric properties permitting lateral movement of the first portions of the valve wall relative to the axis of the cannula;

a first septum valve included in the first portions of the valve wall and having portions defining an opening through the first septum valve, the opening being formed around a second axis;

a second septum valve included in the first portions of the valve wall and having portions defining a second opening through the second septum valve, the second opening being formed around a third axis; and at least one of the second axis of the first septum valve and the third axis of the second septum valve being offset from the first axis of the cannula.

13. The trocar assembly recited in claim 12 further comprising:

a rigid portion of the valve housing fixed to the cannula at the proximal end of the cannula;

a second portion of the valve wall disposed between the first portions of the valve wall and the rigid portions of the valve housing, the second portion of the valve wall disposed in a generally axial relationship with the axis of the cannula; and the second portion of the valve wall having elastomeric properties permitting lateral movement of the first portions of the valve wall relative to the axis of the cannula.

14. The trocar assembly recited in claim 12 further comprising:

means for flexibly coupling the valve wall to the housing to permit the second axis of the first septum valve to move from a first position wherein the second axis of the first septum valve is offset from the first axis of the cannula, to a second position wherein the second axis of the first septum valve is aligned with the first axis of the cannula.

15. The trocar assembly recited in claim 12 wherein both the second axis of the first septum valve and the third axis of the second septum valve are offset from the first axis of the cannula.

16. The trocar assembly recited in claim 12 wherein the first septum valve is a zero closure septum valve.

17. The trocar assembly recited in claim 12 further comprising a third valve having zero closure characteristics and being disposed in the valve housing between the first septum valve and the cannula, the third valve forming with the first septum valve a valve set.

18. The trocar assembly recited in claim 12 wherein the first septum valve is disposed generally in a first plane, the second septum valve is disposed generally in a second plane, and the first plane is generally coplanar with the second plane.

19. The trocar assembly recited in claim 13 wherein:

the first portions of the valve wall form an end wall of the valve housing;

the second portions of the valve Wall form a lateral wall of the valve housing;

the lateral wall is integral with the end wall and forms with the end wall a flexible portion of the valve housing; and the flexible portion of the valve housing is disposed proximally of the rigid portion of the valve housing.

20. The trocar assembly recited in claim 12, wherein the housing comprises:

a first housing portion with rigid walls having the configuration of a first cylinder extending coaxially with the axis of the cannula;

a second housing portion coupled to the first housing portion and forming with the first housing portion a valve housing;

the second housing including a side wall and an end wall;

the first septum valve being formed in the end wall of the second housing portion;

the second septum valve being formed in the end wall of the second housing portion; and the side wall of the second housing portion having flexible characteristics permitting lateral movement of the first septum valve and the second septum valve relative to the axis of the cannula.

21. The trocar assembly recited in claim 20 wherein the first septum valve and the second septum valve are integral with the end wall of the second housing portion.

22. The trocar assembly recited in claim 21 wherein the first septum valve and the second septum valve and the end wall of the second housing portion are disposed generally in a common plane.

23. The trocar assembly recited in claim 21 wherein the side wall of the second housing portion is formed integral with the end wall of the second housing portion, and is coupled to the rigid walls of the first housing portion.

24. A trocar adapted to extend across a body wall into a body cavity, and to form a seal around an instrument inserted through the trocar into the body cavity, the trocar comprising:

- a cannula having a first axis extending between a proximal end and a distal end;
- a valve housing disposed proximally of the cannula in a fixed relationship with the cannula, the valve housing forming with the cannula a working channel of the trocar;
- a septum valve disposed along the working channel of the trocar and forming an opening having a second axis, the septum valve being formed of an elastomeric material stretchable between a first natural position wherein the opening of the septum valve is disposed with the second axis offset from the first axis and of the cannula and a second stretched position wherein the second axis of the septum valve is generally aligned with the first axis of the cannula; and
- means for supporting the septum valve relative to the cannula to prevent movement of the septum valve from the first natural position to the second stretched position without substantial deformation of the opening of the septum valve.

25. The trocar recited in claim 24 further comprising:

- a zero closure valve forming a valve set with the septum valve;
- the zero closure valve being disposed along the working channel between the septum valve and the cannula; whereby
- the instrument passing through the septum valve also passes through the zero closure valve prior to entering the cannula.

* * * * *